United States Patent [19]
Thomas et al.

[11] Patent Number: 5,605,692
[45] Date of Patent: Feb. 25, 1997

[54] EXPRESSION OF STRUCTURAL (P1) REGION OF 1 HEPATITIS A VIRUS BY VACCINIA IN CELL CULTURE FOR USE IN VACCINES

[75] Inventors: Howard C. Thomas; Peter Karayiannis, both of London, England

[73] Assignee: Imperial College of Science, Technology and Medicine, London, England

[21] Appl. No.: 916,149
[22] PCT Filed: Feb. 4, 1991
[86] PCT No.: PCT/GB91/00163

§ 371 Date: Jul. 31, 1992

§ 102(e) Date: Jul. 31, 1992

[87] PCT Pub. No.: WO91/11460

PCT Pub. Date: Aug. 8, 1991

[30] Foreign Application Priority Data

Feb. 2, 1990 [GB] United Kingdom .................. 9002387

[51] Int. Cl.$^6$ ..................... A61K 39/29; A61K 39/125; A61K 39/285; C12N 7/01; C12N 15/51
[52] U.S. Cl. .................... 424/192.1; 424/199.1; 424/226.1; 536/23.72; 435/235.1; 435/320.1
[58] Field of Search .......................... 424/88, 89, 199.1, 424/189.1, 226.1, 192.1; 435/235.1, 320.1; 536/23.1, 23.72

[56] References Cited

FOREIGN PATENT DOCUMENTS

| 154587 | 9/1985 | European Pat. Off. . |
| 0276330 | 7/1987 | European Pat. Off. ........ C12N 15/00 |
| 8800973 | 2/1988 | WIPO . |

OTHER PUBLICATIONS

Anderson, P. A. et al. 1985. Intervirology vol. 24 pp. 26–32.
Locarnini, S. A. et al. 1981. J. Virology vol. 37 pp. 216–225.
Gauss–Müller, V. et al. 1984. Virology vol. 137 pp. 182–184.
Tartaglia, J. et al. 1990. Critical Reviews in Immunology vol. 10 pp. 13–30.
J. et al, J. Virol. 65(5): 2595–2600.
Muckett et al; J. Gen. Vir. 62:2067–82. 1986.
Ostermayr et al, J. Vir. 61(11): 3645–47, 1987.
Ostermayr et al, Vir. Her & Liver Dis., Publ Alan Liss, 1988, pp. 59–61.
Ross et al, Vir Her & Liver Dis, Publ Alan Liss, 1988, pp. 62–64.
Ping et al, PNAS 85: 8281–85, 1988.
Emini et al, J. Vir. 55(3): 836–39. 1985.
Ferg et al, Chin. J. Vir. 5(4):303–311. 1989.
Johnston et al, J. Infect. Dis, 157(6):1203–11. 1988.
Powdrill et al., J. Virol. 65(5): 2686–2690 (1991).
Karayiannis, et al., Vaccination of tamarins with a recombinant vaccinia–hepatitis A virus (HAV) protects against HAV infection, *J. Gen. Virol.* (1991) 72:2167–2172.
Alexander, et al., Regulated Expression of Foreign Genes in Vaccinia Virus unde the Control of Bacteriophage T7 RNA Polymerase and the *Escherichia coli lac* Repressor, *J. Virol.* (1992) 66:2934–42.
Schmidt, et al., The Cytomegalovirus Enhancer: a Pan–Active Control Element in Transgenic Mice *Mol. Cell Biol.* (1990) 10:4406–4411.
Winokur, et al., Journal of Virology (1991) 65(9):5029–5036.

*Primary Examiner*—Mary E. Mosher
*Attorney, Agent, or Firm*—Edward S. Irons

[57] ABSTRACT

An isolated polypeptide comprising a substantially antigenic part of at least one hepatitis A virus epitope, the polypeptide being free from infectious material. The polypeptide is the expression product of a DNA molecule which has been incorporated into a virus, preferably vaccinia virus, using recombinant DNA technology. This expression product, of the recombinant virus containing the DNA molecule coding for it, may be incorporated into a vaccine for immunising against hepatitis A virus.

19 Claims, 4 Drawing Sheets

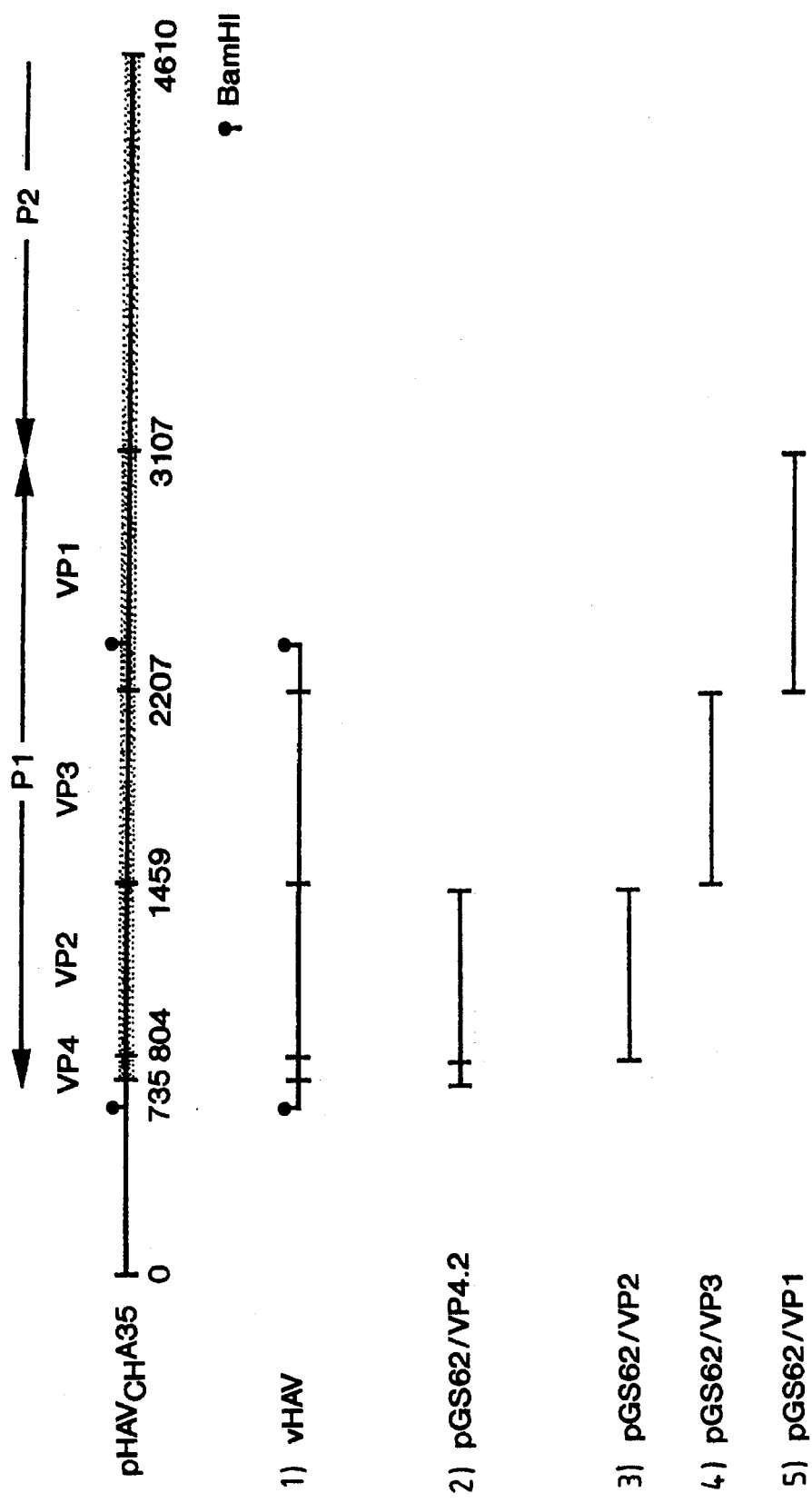

EXPRESSION OF STRUCTURAL (P1) REGION OF 1 HEPATITIS A VIRUS BY VACCINIA IN CELL CULTURE FOR USE IN VACCINES

This invention relates to the prevention of hepatitis and is particularly concerned with the production of new materials suitable for incorption into a vaccine for the prevention of hepatitis A.

Infection with hepatitis A virus (HAV) remains an important cause of morbidity and occasionally mortality, both in countries where it is endemic and in the industrialised nations where it is normally sporadic. As sanitary conditions have been improving in developing countries, the prevelance of HAV seropositivity has been decreasing so creating a large pool of susceptible individuals. These individuals together with high risk groups such as day-care centre staff, parents and siblings of toddlers attending such centres, promiscuous homosexual men and military personnel and tourists in endemic areas would benefit from an effective HAV vaccine.

Hepatitis A virus is classified as a picornavirus with a single strand positive sense RNA genome coding for a single polyprotein which is subsequently processed into structural and nonstructural proteins. The structural proteins are divided into polypeptides, for example VP1, VP2, VP3 and VP4 which form the capsid polypeptides of the virus. There appears to be only one serotype and significant antigenic variation has not been recognised among different HAV strains.

Replication of the virus in tissue culture is slow and yields are poor, thus making the large scale production for vaccines difficult and expensive. Formalin inactivated (Provost et al, *J. Med. Virol.*, 1986, 19, 23–31. Binn et al., *J. Infect. DIS*, 1986, 153, 749–756.) and live attenuated virus vaccines (Provost et al., *Proc. Soc. Exp. Biol. Med*, 1982, 170, 8–14. Karron et al., *J. IneCt, Dis*, 1988, 157, 338–345.) have been produced and shown to be protective both in primates and human volunteers. Problems of large scale production and stability of these vaccines in man need to be overcome and the safety and durability of immunity still have to be established. Moreover, one disadvantage of these vaccines is that 3 doses of vaccine are required to produce an adequate anti-HAV response.

A candidate sub-unit vaccine based on the VP1 structural polypeptide has been produced by recombinant DNA techniques in *E. coli* and used to immunize rabbits (Johnston et al., *J. Infect. Dis*, 1988, 157(6), 1203–1211). The resulting antibody reacted only with denatured VP1 and not with intact HAV, indicating that the conformational epitope had not been expressed by the *E. Coli*.

It has now been found that a valuable vaccine material can be produced by incorporating at least part of the HAV genome in a vaccinia virus, using recombinant DNA technology. The polypeptide expressed by the vaccinia virus is capable of evoking a protective immune response following only a single injection of the material.

According to one aspect of the invention there is provided an isolated polypeptide comprising a substantially antigenic part of at least one HAV epitope, free from infectious material.

The isolated HAV polypeptide may comprise all or part of VP1, either alone or together with VP3, or all or part of VP3 alone. Alternatively, the polypeptide may comprise all or part of VP1 together with VP4, VP2 and VP3, or at least two HAV structural proteins selected from VP1 to VP4 inclusive.

According to a second aspect of the invention there is provided a DNA molecule comprising a nucleotide sequence substantially coding for all or a portion of at least one HAV structural polypeptide.

The nucleotide sequence of the DNA molecule may code for, all or a part of HAV VP1, either alone or together with VP3, or all or part of VP3 alone. Alternatively the nucleotide sequence may code for all or part of VP1 together with VP4VP2 and VP3, or at least two HAV structural polypeptides selected from VP1 to VP4 inclusive.

The DNA molecule may also comprise a viral promotor operatively linked to the nucleotide sequence.

In yet a further aspect of the invention there is provided a virus genetically engineered to express all or a part of at least one HAV structural polypeptide.

The virus to be genetically engineered may be selected from vaccinia, herpes, papovaviruses such as SV40, papillomaviruses, adenoviruses, retroviruses and baculoviruses, but other viruses not listed here may also be used.

Such genetically engineered recombinant viruses may be incorporated into a vaccine suitable for immunising mammals, in particular man, against hepatitis A infections. Alternatively the vaccine may comprise the proteins expressed by such viruses.

The insertion into a virus, in particular a vaccinia virus, of an HAV cDNA fragment coding for example for the structural proteins VP4, VP2, VP3 and at least some of VP1 (57 amino acids from the amino end) involves preparing the required cDNA using for example the method described by Ticehurst et al in *PNAS*, 1983, 80, 5885–5889. Alternatively the required cDNA may be derived from one of the recombinant plasmids described by Ticehurst (see above) using restriction endonuclease digestion. In this way, a 1742 base pair cDNA fragment of HAV encoding the structural polypeptides may be readily obtained usina Sam Hi digestion. Using map positions in Baroudy et al., *PNAS*, 1985, 82, 2143–2147 a fragment covering positions 611 to 2353 of the HAV genome can be obtained.

However, the present invention is not necessarily restricted to the incorporation of such Bam H1 fragments of HAV into vaccinia but extends to the incorporation of smaller fragments or different fragments encoding some or all of the VP1, VP2, VP3 and VP4 regions. One combination of particular interest is DNA encoding both the VP1 and VP3 regions, as these regions are believed to contain the immunodominant epitope of the virus, and may also contain the cytotoxic T-cell epitopes. Such DNA fragments can be prepared from larger portions of DNA utilising appropriate restriction enzymes, or alternatively can be synthesised using the polymerase chain reaction with appropriate primers (Bell, *Immunology Today*, 1989, 10(10), 351–355).

Once prepared, the selected HAV cDNA is inserted into a plasmid vector capable of homologous recombination with a viral genome. Suitable plasmids are described by Mackett et all in J. Virol., 1984, 49(3), 857–864.

The methods for the incorporation of heterologous DNA into vaccinia virus are now well-known and such methods are used in the present invention (see Mackett et al in DNA Cloning ed. Glover (IRL Press, Oxford) Vol. II, 191–211, 1985). Briefly, these involve the introduction of the heterologous DNA encoding the desired HAV epitopes into a plasmid vector of vaccinia downstream of the vaccinia promotor so that it is flanked by the vaccinia TK sequences and introducing the resultant recombinant vector into cells infected with vaccinia virus. By recombination between the vector containing the HAV sequences and the homologous sequence in the vaccinia genome it is possible to generate a TK recombinant virus which is capable of expressing the heterologous gene. The techniques that have been used for the incorporation of other heterologous genes into vaccinia virus are described for example in Kieny et al, *Nature*, 1984, 312, 163–166 (1984); Wiktor et al, PNAS 81, 7194–7198 (1984); Moss eL al, Nature 311, 67–69(1984); Mackett et al, Science, 227, 433–435 (1985); Elango et al, PNAS, 83, 1906–1910 (1986) and Mackett et al, B. J. Virol. 48, 857–864 (1984); and reference may be made to any of these documents for further guidance.

A particularly convenient method involves transfection of mammalian cells infected with vaccinia virus. The use of the recombinant techniques described results in part of the functional TK gene of the wild type vaccinia virus being replaced by the non-functional TK gene sequence within which is incorporated the DNA encoding the HAV epitope. The recombinant virus is TK-and can therefore be selected with 5-bromodeoxyuridine.

It has been found that when the cDNA fragment of HAV encoding at least one HAV structural polypeptide is expressed under the control of the vaccinia promotor, the expressed polypeptide is not merely the desired HAV capsid polypeptide but is polypeptide that appears to fold in the correct manner to form the conformational epitope.

Most tissue cell lines are capable of supporting the Growth of vaccinia virus, for example CV1 cells as well as Vero cells, human lymphoid and diploid cells and TK- cells (human and mouse) can be used. For large scale production of virus HeLa S3 spinner cells seem to give the best yields.

The recombinant vaccinia virus in accordance with the present invention is capable of expressing HAV polypeptide as a fusion product. There is no termination codon at the end of the 1.7 kb HAV fragment. Transcription continues into the interrupted TK gene until a termination codon is encountered. The expected length of the fusion protein would be about 65000 Daltons, as the interrupted TK gene is in frame with the HAV insert. Translation ends at the TK gene termination codon. This has been confirmed by Westernblot analysis, by immuno-staining of vaccinia infected cell monolayers and by radioimmunoassay. In the latter case positive to negative ratios of 5 were obtained. The HAV proteins expressed by the recombinant vaccinia virus have been found capable of affording protection against subsequent challenge by HAV. The immunity provided by the HAV proteins expressed by the genetically engineered or recombinant vaccinia virus, when injected into a susceptible host, may be both cell mediated, that is T-cell mediated and humoral. Consequently, such HAV proteins are of value in a protective vaccine. The present invention therefore includes a vaccine composition comprising the recombinant vaccinia virus according to the present invention either as inactivated whole or live virus. Alternatively, the vaccine may comprise an isolated HAV as hereinbefore described. Such a vaccine will normally be formulated in a sterile aqueous medium that will be pyrogen-free for parenteral administration, e.g. by the subcutaneous, intradermal, intravenous and intramuscular routes or by scarification.

The purified (virus-free) recombinant antigenic protein expressed in tissue culture by the recombinant virus can also be used as a vaccine. Similarly, the same gene product for vaccine production (with or without downstream TK sequences) could be inserted into suitable expression vectors for expression in prokaryotic cells or baculoviruses for expression in insect cells.

The recombinant proteins of the present invention are also of use in the production of antibodies, either monoclonal or polyclonal, obtainable by conventional hybridoma or serum raising methods. Such antibodies are useful either in passive immunisation or as diagnostic agents.

In the accompanying drawings:

FIG. 4 shows the structural region of HAV genome and chimeras containing coding sequences for the structural polypeptides.

Figure 1:
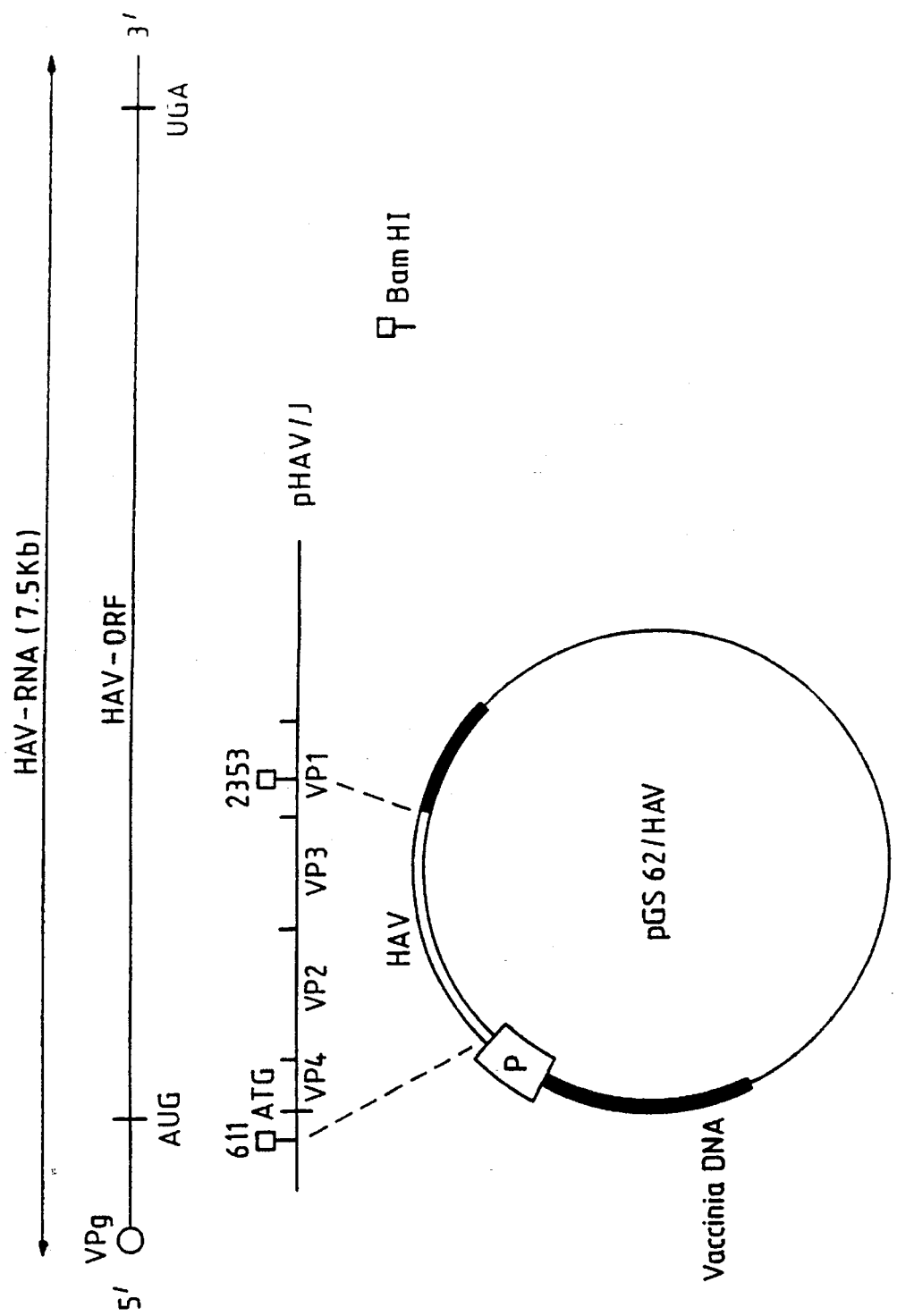
FIG. 1 shows the contruction of the recombinant vaccinia virus in accordance with Example 1.

The invention will be further described by way of reference to the following examples:

EXAMPLE 1

Preparation Of Recombinant Vaccinia Virus

An insertion vector, pGS 62 containing a vaccinia virus early promotor (7.5K) (Ticehurst et al., *J. Clin. Microbiol,* 1987, 25, 1822–1829) was linearised with Sam H1 endonuclease digestion followed by phosphatase treatment. A Bam Hi fragment from plasmid pHAV/J (Karayiannis et al., Viral Hepatitis and Liver Disease ed. Zuckerman (Alan R. Liss New York 1988) 117–120) and covering position 611 to 2353 of the HAV genome, was ligated with the linearised pGS 62 immediately after the 7.5K promotor to form the chimeric plasmid pGS 62/HAV. There were 101 nucleotides for the 5' untranslated region of the HAV genome between the cloning site and the ATG to the HAV open reading frame coding for the polyprotein. The remainder of the genome codes for the structural polypeptides VP4, VP2, VP3 and the first 57 amino acids of the amino terminal end of VP1. *E. coil* colonies from transformed bacteria carrying the chimeric plasmid were identified by hybridisation to a 32P-labelled HAV cDNA probe and the correct orientation of the insert, with respect to the vaccinia 7.5K promotor, was determined by dideoxynucleotide sequencing.

The construction of the chimera is set out in detail in FIG. 1 of the accompanying drawings. The resulting chimeric plasmid was transfected into Vero cells in tissue culture using standard procedures. The same cultures were then infected with wild-type vaccinia. Genetic recombination occurs between homologous regions in the plasmid and wild-type vaccinia virus DNA resulting in the interruption of the thymidine kinase (TK) gene. The resultant TK recombinant viruses were selected as described in Mackett et al, Chapter 7, DNA Cloning, Vol. II (D. M. Glover, Ed. IRL Press Oxford, 1985, 191–211). The presence of the foreign gene in the recombinant vaccinia virus was confirmed by dot-blot hybridisation (Karayiannis et al., Viral Hepatitis and Liver Disease, ed. Zuckerman, A. J. (Alan R. Liss, New York) 117–211) and Southern blot analysis (Mackett et al., see above) using 32P-labelled HAV cDNA probes.

Expression of HAV polypeptides was established by a solid phase RIA (Karayiannia et al, *J. Med. Virol.,* 1986, 18, 261–276) of cell lysates and by immunostaining of virus infected monolayers with human anti-HAV. Detection of plaques expressing HAV polypeptides was achieved by using rabbit anti-human and swine anti-rabbit antisera in turn. The latter was labelled with biotin and alkaline phosphatase (DAKOPATTS, ABComplex.AP, Denmark).

EXAMPLE 2

Preparation and Testing of HAV Vaccine

A vaccine was prepared using the recombinant virus obtained as described in Example 1. The vaccine was formulated with recombinant virus suspended in Gibco-BRL's RPMI medium 1640 (a growth medium that does not contain foetal calf serum) so that 0.1 ml of the vaccine contained $10^8$ plaque forming units (PFU). The tests were carried out on three tamirins, *Saguinus labiatus.* Two of the animals were innoculated intradermally with $10^8$ PFU in the upper part of their back while the third animal was innoculated with a similar formulation containing $10^7$ PFU of wild-type vaccinia virus.

Prior to vaccination, the serum samples from all three animals were negative for anti-HAV antibody. Serum from all three animals was tested again for anti-HAV antibody nine weeks after vaccination, the two animals innoculated with the vaccine of the invention had detectable anti-HAV antibody titres of $1/40$ and $1/100$.

Figure 2:
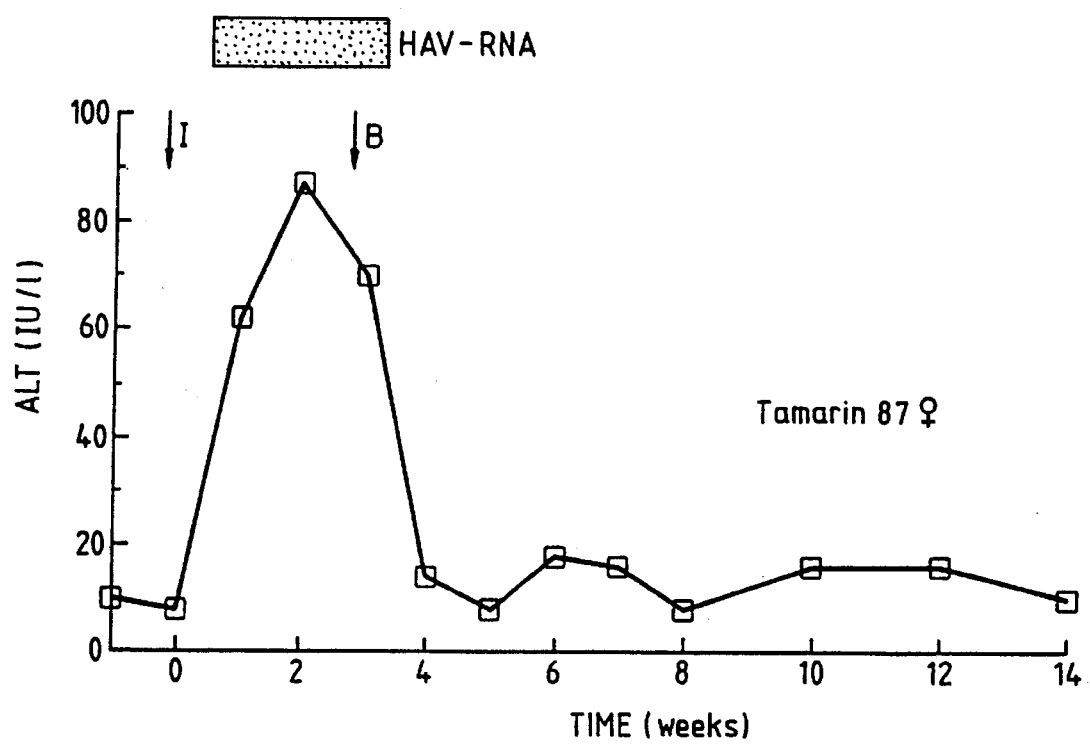
FIG. 2 shows the ALT profile for an unvaccinated tamarin as described in Example 2 below.
Figure 3A:
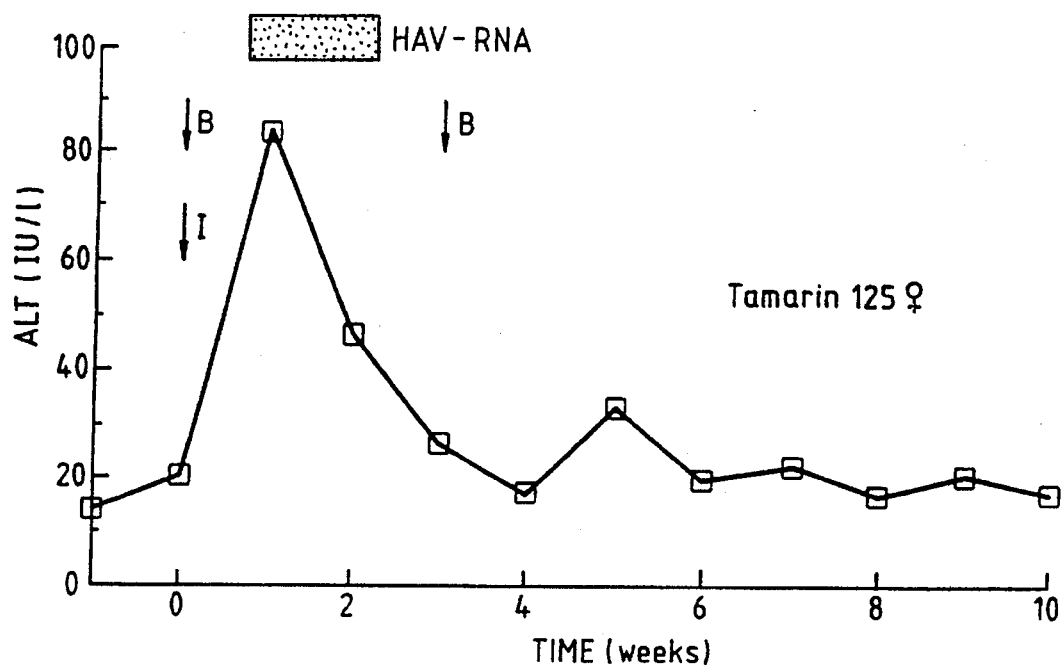
FIGS. 3A and 3B show ALT profiles for tamarins vaccinated with wild-type vaccinia virus of the vaccine of the invention, as described in Example 2 below.
Figure 3B:
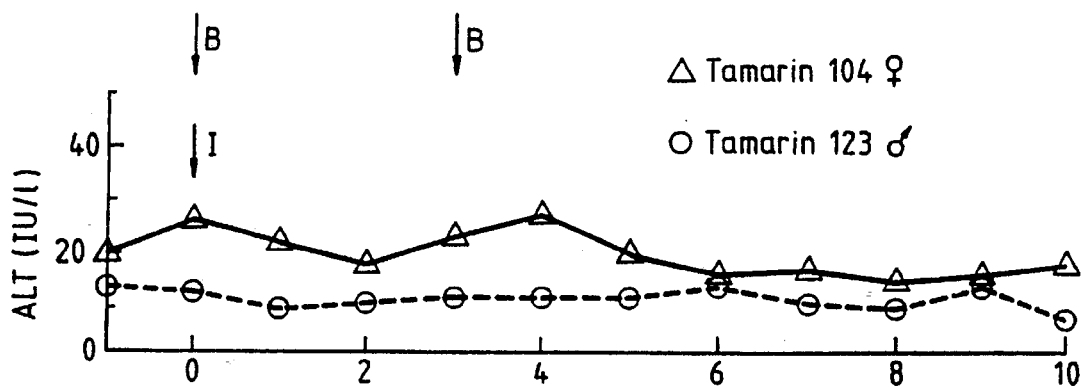

Ten weeks after vaccination, all three animals were challenged intravenously with 0.4 ml live HAV strain HM 175 grown in tissue culture. The disease profile with this innoculum was predetermined in a fourth tamarin, the results being shown in FIG. 2 of the accompanying drawings. FIG. 3 of the accompanying drawings shows that tamarin 125, vaccinated with wild-type virus, developed the expected changes similar to those illustrated in FIG. 2. The ALT (alanine aminotransferase) elevation lasted from weeks 1 to 3. In contrast, the two animals vaccinated with the vaccine of the invention did not show any ALT elevations. Their ALT levels fluctuated at about their pre-challenge value. The two animals protected with the vaccine of the invention showed no histological changes in their liver biopsies performed three weeks after challenge. Preinnoculation biopsies were normal in all three animals. However, the liver biopsy of the unprotected animal 125, taken during the acute phase of the hepatitis, showed predominantly cytopathic changes.

IgM anti-HAV antibody was detected in the control animal 125 from weeks 2 to 6. No IgM anti-HAV response was detected in the animals protected by the vaccine of the invention, but there was a secondary response following challenge with the live virus. The titres rose to $10_2$ and $10_3$ for each protected animal respectively within a week of challenge and remained at those levels throughout the period to follow up. In control animal 125, anti-HAV titres did not plateau until week 6.

These results show that the vaccine of the invention not only elicited an immune response to HAV structural polypeptide but subsequently protected the animal when challenged with a live HAV strain capable of inducing hepatitis as demonstrated in the two unprotected animals.

EXAMPLE 3

Preparation of HAV structural polypeptides

In order to determine the role of the four structural polypeptides (VP1, VP2, VP3, VP4) of the hepatitis A virus in eliciting an immune response, further chimeras were prepared using the method described in Example 1, for the generation of the relevant recombinant vaccinia viruses.

As shown in FIG. 4, chimeras were constructed containing the coding sequence for individual structural polypeptides or combinations of these. The coding sequences were generated using the polymerase chain reaction with the appropriate primers. The 5' end primer contained an initiation codon (ATG) ensuring in frame translation of the relevant polypeptide.

Using chimeras 1), 2) and 5) recombinant vaccinia viruses were generated and tested for immunogenicity by injection into rabbits and by radioimmunoassay using polyclonal antibodies.

Prior to inoculation with recombinant vaccinia virus, serum samples from all rabbits are negative for anti-HAV antibody. Serum from all rabbits is tested again for anti-HAV antibody and all show detectable anti-HAV antibody to varying degrees.

EXAMPLE 4

Detection of cell mediated immunity

Cell lines, either fibroblast or lymphoblast cells from tamarins are established using known techniques and then transformed. Following establishment, the cell lines are infected with various of the recombinant viruses shown in FIG. 4.

Lymphocytes from tamarins infected with virulent HAV virus are obtained and added to cultures of the cell lines described above. Release of radioactive chromium from the target cells is indicative of cytotoxic T-cell mediated mechanisms. In order to detect the presence of cell mediated immunity, cell killing is looked for, as evidenced by the release of labelled chromium.

Killing of the lymphocytes from infected tamarins is detected to varying degrees by cell lines infected with recombinants 1, 2, 3, 4 and 5.

The plasmid pGS62/HAV was deposited on Sep. 12, 1996 at the ECACC located in Salisbury, Wiltshire, England and assigned Accession Number V96091243.

We claim:

1. A polypeptide comprising the sequence of hepatitis A virus (HAV) VP4, VP2, VP3, and part but not all of VP1, wherein said part of VP1 comprises at least the 57 amino acids from the amino terminal end of VP1.

2. A polypeptide as claimed in claim 1, wherein said HAV sequence is fused to part but not all of a viral thymidine kinase sequence.

3. A polypeptide as claimed in claim 2, wherein the thymidine kinase is vaccinia virus thymidine kinase.

4. A polypeptide as claimed in claim 2, wherein said polypeptide does not include the sequence of non-structural proteins of HAV.

5. A DNA molecule comprising a nucleotide sequence coding for a polypeptide comprising the sequence of HAV VP4, VP2, VP3, and part but not all of VP1, wherein said part of VP1 comprises at least the 57 amino acids from the amino terminal end of VP1; wherein said polypeptide does not include the sequence of nonstructural proteins of HAV.

6. A DNA molecule as claimed in claim 5, further comprising a viral promoter operatively linked to the nucleotide sequence.

7. A DNA molecule as claimed in claim 6, wherein the promoter is a vaccinia virus promoter.

8. A virus which expresses the polypeptide of claim 1, 2, 3, or 4.

9. The virus of claim 8, which is vaccinia virus.

10. A virus which contains a DNA molecule according to claim 5, 6, 7.

11. The virus of claim 10 which is vaccinia virus.

12. An immunogenic composition comprising the polypeptide of any of claims 1–4.

13. An immunogenic composition comprising the virus of claim 8.

14. An immunogenic composition comprising the virus of claim 9.

15. An immunogenic composition comprising the virus of claim 10.

16. An immunogenic composition comprising the virus of claim 11.

17. A vaccine comprising the virus of claim 9.

18. A vaccine comprising the virus of claim 11.

19. The plasmid PGS 62 /HAV.

* * * * *